US008956591B2

(12) United States Patent
Ishikawa et al.

(10) Patent No.: US 8,956,591 B2
(45) Date of Patent: Feb. 17, 2015

(54) METHOD FOR DETECTING CANCER USING ICG FLUORESCENCE METHOD

(75) Inventors: Osamu Ishikawa, Osaka (JP); Terumasa Yamada, Osaka (JP); Kunihito Gotoh, Osaka (JP); Mitsuharu Miwa, Hamamatsu (JP); Takahiro Shikayama, Hamamatsu (JP)

(73) Assignees: Osaka Prefectural Hospital Organization, Osaka-shi, Osaka (JP); Hamamatsu Photonics K.K., Hamamatsu-shi, Shizuoka (JP)

( * ) Notice: Subject to any disclaimer, the term of this patent is extended or adjusted under 35 U.S.C. 154(b) by 795 days.

(21) Appl. No.: 12/466,085

(22) Filed: May 14, 2009

(65) Prior Publication Data

US 2009/0285760 A1     Nov. 19, 2009

Related U.S. Application Data

(60) Provisional application No. 61/053,249, filed on May 15, 2008.

(51) Int. Cl.
*A61B 5/00*     (2006.01)
*A61K 49/00*     (2006.01)
*G01N 21/64*     (2006.01)

(52) U.S. Cl.
CPC ............. *A61B 5/0059* (2013.01); *A61B 5/4244* (2013.01); *A61B 5/445* (2013.01); *A61K 49/0034* (2013.01); *G01N 21/6428* (2013.01); *G01N 21/6456* (2013.01)
USPC ........................................................ 424/9.6

(58) Field of Classification Search
None
See application file for complete search history.

(56) References Cited

U.S. PATENT DOCUMENTS

| 5,699,798 | A | 12/1997 | Hochman et al. | |
| 5,827,190 | A | 10/1998 | Palcic et al. | |
| 2006/0108509 | A1* | 5/2006 | Frangioni et al. | 250/208.1 |

FOREIGN PATENT DOCUMENTS

| CN | 1976639 | 6/2007 |
| JP | 9-309845 | 12/1997 |
| JP | 2001-299676 | 10/2001 |
| JP | 2002-95663 | 4/2002 |
| JP | 2003-290128 | 10/2003 |
| JP | 2004-255180 | 9/2004 |
| JP | 2004-538485 | 12/2004 |
| JP | 2006-509573 | 3/2006 |
| JP | 2007-533737 | 11/2007 |
| WO | WO 0074727 A2 * | 12/2000 |
| WO | 2006/003762 | 1/2006 |

OTHER PUBLICATIONS

Michael Gurfinkel et al., "Pharmacokinetics of ICG and HPPH-car for the Detection of Normal and Tumor Tissue Using Fluorescence, Near-infrared Reflectance Imaging: A Case Study," Photochemistry and Photobiology, 2000, vol. 72, pp. 94-102.
Susumu Ito et al., "Principle and clinical usefulness of the infrared fluorescence endoscopy," The Journal of Medical Investigation, Feb. 2006, vol. 53, pp. 1-8.
Yoshinaga et al., "Micrometastasis of Breast Cancer in the Sentinel Lymph Nodes," Med. Bull. Fukuoka University, vol. 37(2), pp. 67-72, 2010.
Sawicki et al., "Sentinel lymph node detection with the use of SPECT-CT in endometrial cancer—analysis of two cases," Ginekologia Polska, 2012, 83, Nr. 9, pp. 703-707.
Kitai et al., "Fluorescence Navigation with Indocyanine Green for Detecting Sentinel Lymph Nodes in Breast Cancer," Breast Cancer, vol. 12, No. 3, Jul. 2005, pp. 211-215.
European Search Report dated Jun. 5, 2012 issued in counterpart European Patent Application No. 09746672.6 (8 pages).
Takeshi Aoki et al, "A novel method for identification of liver segment using image-guided fluorescence navigation system with indocyanine green", Surgical Therapy, Japan, Nagai Shoten, vol. 96, No. 6, Jun. 1, 2007, p. 1047-p. 1049 (Partial English translation of highlighted portions is attached).
Naoyuki Yokoyama et al, "Gallbladder Cancer Operation Using the ICG-Near-Infrared Light System", Operation, Japan, Kanehara & Co., Ltd, vol. 62, No. 5, May 15, 2008, p. 613-p. 618 (Partial English translation of highlighted portions is attached).

* cited by examiner

*Primary Examiner* — Michael G Hartley
*Assistant Examiner* — Jennifer Lamberski
(74) *Attorney, Agent, or Firm* — Drinker Biddle & Reath LLP

(57) ABSTRACT

A method of detecting an accessory cancer lesion, comprising an administration step wherein indocyanine green is administered to a living body, an irradiation step wherein a target organ suspected of having cancer is surgically exposed and irradiated with excitation light of indocyanine green, an imaging step wherein a near-infrared fluorescence intensity distribution image from the excited indocyanine green in the target organ is obtained, and an identification step wherein an area having the near-infrared fluorescence in the intensity distribution image, excluding the area detected in preoperative examination or intraoperative macroscopic observation, is identified as an accessory cancer lesion.

8 Claims, 7 Drawing Sheets

METHOD FOR DETECTING CANCER USING ICG FLUORESCENCE METHOD

This application claims the benefit of U.S. Provisional Application No. 61/053,249, filed May 15, 2008.

BACKGROUND OF THE INVENTION

1. Field of the Invention

The present invention relates to a method of detecting cancer using an ICG fluorescence method. The present invention further relates to a method of detecting an accessory cancer lesion and a device used thereof, a method of treating the cancer, and an accessory cancer lesion detection agent and composition thereof.

2. Related Background Art

Computer tomography (CT), nuclear magnetic resonance imaging (MRI), and ultrasonographic imaging are widely used as methods of imaging a cancer lesion. For example, contrast CT, wherein an iodinated contrast agent having high x-ray absorption is injected into a blood vessel (normally a peripheral vein), is generally used for testing cancer by CT (see, for example, National Publication of International Patent Application No. 2007-533737).

SUMMARY OF THE INVENTION

However, even when the cancer lesion is identified by a method described above, or any other known imaging method, and resected, this does not lead to complete cure of the cancer in many cases.

For example, the 5-year recurrence-free survival of patients who have undergone radical resection of hepatocellular carcinoma (HCC) is as low as about 30%. One suspected reason for this low survival, especially in cases of early recurrence that occurs within 2 years post surgery is that the accessory cancer lesion that cannot be detected by conventional preoperative examination or intraoperative macroscopic observation is missed in the resection. Thus, there is a need to improve the sensitivity of detecting the accessory lesion before and during the surgery, in order to completely cure the cancer.

The object of the present invention is therefore to provide a detection method that enables the detection of an accessory cancer lesion.

The present invention provides a method of detecting an accessory cancer lesion, comprising an administration step wherein indocyanine green (ICG) is administered to a living body, an irradiation step wherein a target organ suspected of having cancer is surgically exposed and irradiated with indocyanine green excitation light, an imaging step wherein a near-infrared fluorescence intensity distribution image from the excited indocyanine green in the target organ is obtained, and an identification step wherein an area having the near-infrared fluorescence in the intensity distribution image, excluding the area detected in preoperative examination or intraoperative macroscopic observation, is identified as an accessory cancer lesion.

By employing this method, an accessory cancer lesion can be detected intraoperatively in an area where it has not been detected by x-ray (CT), MRI, ultrasonography, or macroscopic observation of the target organ. Therefore, the method can prevent the missing of a minute accessory cancer lesion during surgery, and improve postoperative survival. In the present invention, the lesion detected by preoperative examination (x-ray, MRI, ultrasonography, etc) or through intraoperative macroscopic observation is termed "main cancer lesion".

A conventional test for liver function is performed wherein indocyanine green (a dye) is injected into a vein in the arm, blood is collected after the lapse of a certain time, the residual dye in the blood is quantitatively determined, and the amount of dye processed by the liver is calculated. However, the present inventors were the first to discover the phenomenon of intravenously injected indocyanine green that is neither complexed with a high density lipoprotein nor has antibodies against proteins specifically present in cancer tissue, accumulating to detectable levels not only in the main lesion but also in the accessory lesion.

The application of the above-described method provides an excellent method of treating cancer. In short, a method of treating cancer by shrinking, destroying or resecting an area containing at least one accessory lesion identified by the method of detecting an accessory cancer lesion can be provided.

It became clear from the above finding that the indocyanine green functions as a detection agent for an accessory cancer lesion. In other words, the indocyanine green that is neither complexed with a high density lipoprotein nor bound to antibodies against proteins specifically present in an accessory lesion effectively functions as an accessory cancer lesion detection agent.

The indocyanine green need not be used alone; it can be used in the form of a distilled water-containing composition, for detecting an accessory cancer lesion.

In other words, the use of the indocyanine green, or a composition containing indocyanine green and distilled water, for detecting an accessory cancer lesion is provided.

Further, the present invention provides a data collection method comprising comparing a near-infrared fluorescence intensity distribution image obtained by irradiating the target organ in a living body into which indocyanine green has been administered with indocyanine green excitation light, with a cancer lesion distribution image obtained by the use of x-rays, nuclear magnetic resonance or ultrasound on the target organ before administering the indocyanine green, and collecting the data of an area that is detected in the near-infrared fluorescence intensity distribution image but not in the cancer lesion distribution image as accessory cancer lesion area data.

According to this method, the data on the accessory cancer lesion (including boundary information, such as location, size, etc, of the accessory cancer lesion) can be collected from an area of the target organ that are not detected by x-ray CT, MRI, ultrasonography, or macroscopic observation. In other words, the data collection method of the present invention is a method of collecting data on a human body for assisting the final diagnosis. The use of such data can prevent the missing of a minute accessory cancer lesion by doctors, and improve the postoperative survival of the patient. In the present invention, a lesion detected in the cancer lesion distribution images obtained by the use of x-rays, MRI, or ultrasound on the target organ before administering the indocyanine green is termed "main cancer lesion".

It is preferable to obtain the near-infrared fluorescence intensity distribution image of the target organ after intravenous injection of indocyanine green, and it is preferable to obtain the intensity distribution image of the target organ 1 to 10 days after indocyanine green administration.

Furthermore, it is preferable to obtain the near-infrared fluorescence intensity distribution image of the target organ in a living body administered with indocyanine green that is neither complexed with a high density lipoprotein nor bound to antibodies against proteins specifically present in an accessory cancer lesion. However, the near-infrared fluorescence intensity distribution image can also be obtained from a target organ in a living body to which indocyanine green in the form of the above-described complex, or indocyanine green bound to the above-described antibodies, has been administered.

The device described below can be used in the above-described accessory cancer lesion detection method and data collection method. In other words, one can use an accessory cancer lesion detector, which detects an accessory cancer lesion during the surgery for shrinking, destruction, or resection of a cancer lesion, and comprises an irradiation means for irradiating the target organ suspected of having cancer in a living body into which indocyanine green has been administered with indocyanine green excitation light, and an imaging means for obtaining the near-infrared fluorescence intensity distribution image from the excited indocyanine green in the target organ.

In this device, it is preferable that the irradiation means and imaging means are installed in an integrated manner so that the device can be brought close to the site of the accessory lesion exposed by the surgery. This type of configuration enables image acquisition, for instance, by bringing the device close to the cancer lesion after the abdomen has been surgically opened.

EFFECT OF THE INVENTION

The present invention can provide a method of detection that enables the detection of an accessory cancer lesion and a data collection method for an accessory cancer lesion area, and therefore, can improve the 5-year recurrence-free survival of patients who undergo radical cancer surgery.

DESCRIPTION OF THE PREFERRED EMBODIMENTS

A preferred embodiment is described below, referring to the drawings. In the description of the drawings, identical symbols are assigned to the same components, and duplication of descriptions is avoided. Furthermore, parts of the drawings are exaggerated to facilitate better understanding, and the dimensional proportions do not always match with those of the components described.

First, the method of detecting an accessory cancer lesion will be described. The method of detecting an accessory cancer lesion of the present invention comprises the above-described administration step, irradiation step, imaging step, and identification step. Now a preferred embodiment is described stepwise.

In the administration step, indocyanine green is administered to a living body (human or non-human mammal). In this step, normally, the indocyanine green is administered through intravenous injection, and it is preferable for the indocyanine green used in this step to be neither complexed with a high density lipoprotein nor bound to antibodies against proteins specifically present in an accessory cancer lesion. Further, it is preferable to intravenously inject the indocyanine green along with distilled water, in the form of a composition for detecting an accessory cancer lesion. The content of indocyanine green in the accessory cancer lesion detecting composition can be suitably decided, taking into account the type and stage of the cancer, and the age and body weight of patient (or animal patient). It is preferable to carry out this step before starting the surgery for shrinking, destruction, or resection of the cancer.

Next, the irradiation step, wherein indocyanine green excitation light is irradiated on the target organ suspected of having the cancer, is carried out. Near-infrared light (700 to 1000 nm, particularly 700 to 800 nm) is preferable as the excitation light. The use of a light emitting diode (LED) or a semiconductor laser (LD) is preferable as the specific means in the irradiation step. Alternatively, one may use an optical filter (such as a low pass filter that allows the passage of light of wavelength 800 nm or less, or a band pass filter with a center wavelength of 760 nm) fitted to a halogen lamp of about 150 W as the excitation light source, and light from this source may be irradiated through optical fibers. The intensity of the excitation light and the excitation time can be decided suitably, depending on the amount of indocyanine green introduced, the size of the cancer lesion, etc. This step is preferably carried out after the start of the surgery for shrinking, destruction, or resection of the cancer lesion but before carrying out the shrinking, destruction or resection.

Next, the near-infrared fluorescence intensity distribution image from the excited indocyanine green in the target organ is obtained in the imaging step.

The near-infrared fluorescence from the excited indocyanine green typically has a wavelength of 800 to 900 nm (825 to 850 nm in particular). Therefore, the near-infrared fluorescence intensity distribution image is obtained using an imaging means that can capture light of the concerned wavelengths. Examples of such imaging means include solid state imagers such as CCD cameras. When using a CCD camera, it is preferable to remove the infrared cut filter.

The imaging step is preferably carried out 1 to 10 days, more preferably 3 to 5 days, after the indocyanine green administration step. If the imaging is done soon after the administration of the indocyanine green (in less than 1 day from the administration step), sometimes, near-infrared fluorescence is obtained from all parts of the target organ, and there is the possibility of not being able to differentiate the lesion from normal tissue. Beyond 10 days after the administration step, the near-infrared fluorescence sometimes becomes faint even in the lesion.

The present inventors do not wish to adhere to one particular theory, but assume that the indocyanine green gets accumulated in the neovascularized part of the cancer lesion. New blood vessels are continuously formed one after the other in a cancer lesion. It is conceivable that the indocyanine green can easily leak out from the newly formed blood vessels, and therefore, it gets accumulated around the newly formed vessels.

The imaging step is preferably carried out after the start of the surgery for shrinking, destruction, or resection of the cancer lesion but before carrying out the shrinking, destruction or resection. In other words, it is preferable to do the imaging after starting the surgery for treating the cancer, but before actually treating the cancer lesion. As for the surgical method, resection is considered to be most suited for the method of the present invention.

It is suitable to do the imaging 2-dimensionally or 3-dimensionally all over the target organ. In this manner, the location of the cancer lesion (a main lesion and/or an accessory lesion) that are the targets of shrinking, destruction or resection can be accurately identified.

Next, the identification step is carried out. In this step, the area having near-infrared fluorescence, other than the area of the intensity distribution image already detected in the preoperative examination or intraoperative macroscopic observation is identified as the accessory cancer lesion.

In the identification step, the area, other than the area (main lesion) detected by x-ray CT, MRI, ultrasonography, or macroscopic observation of the target organ, can be identified as the accessory lesion. In this case, there may be more than one accessory lesion identified.

The cancer targeted by the present invention is preferably a solid cancer (primary cancer) such as gastric cancer, esophageal cancer, colon cancer, liver cancer, etc, but it can be metastatic cancers that have metastasized from a cancer of some other organ. Among the solid cancers, liver cancer, hepatocellular carcinoma in particular, is suitable for applying the method of the present invention because patients of such cancers have low postoperative survival. Furthermore, the subject (living body) to be tested can be a human or non-human mammal.

A novel method of treating cancer, where the accessory cancer lesion detection method of the present invention is used, is provided. In other words, a method of treating cancer is provided, wherein the area having at least one accessory lesion identified by the accessory cancer lesion detection method is shrunk, destroyed, or resected. In this treatment method, usually, the main cancer lesion is shrunk, destroyed or resected along with the area having at least one accessory lesion.

As described above, the indocyanine green functions as the accessory cancer lesion detection agent. In other words, the indocyanine green functions as a detection agent that detects an accessory lesion present in an area where no lesion is detected in the x-ray imaging, MRI, ultrasonography, or macroscopic observation. As described for the administration step, indocyanine green that is neither complexed with a high density lipoprotein nor bound to antibodies against proteins specifically present in the accessory lesion is suitable.

The accessory cancer lesion detection agent is effective for liver cancer, especially hepatocellular carcinoma. It is preferable to administer it to the living body (human or non-human mammal) at such a time that the detection would be done 1 to 10 days later.

Next, the data collection method of the present invention is described. In the data collection method of the present invention, the near-infrared fluorescence intensity distribution image is obtained by irradiating the target organ in the living body into which indocyanine green has been administered with indocyanine green excitation light. Besides this, a cancer lesion distribution image of the target organ is obtained by the use of x-rays, nuclear magnetic resonance or ultrasound, before administration of the indocyanine green.

The near-infrared fluorescence intensity distribution image from the target organ of a living body to which indocyanine green has been administered can be obtained in above-described mode.

The cancer lesion distribution image is obtained by the use of x-rays, nuclear magnetic resonance or ultrasound to the target organ before the indocyanine green administration. The lesion detected by such imaging is the main cancer lesion, and the detectable size of such lesion is about 5 mm in the long axis direction.

The cancer lesion distribution image obtained by the use of x-rays, i.e., the x-ray image (CT), can be captured using, for instance, the AQUILION 16™ medical x-ray CT system (manufactured by Toshiba Medical Systems Corporation) or similar equipment. The nonlimiting exemplified condition for capturing x-ray image (CT) of a liver is: tube voltage 120 kV, tube current 400 mA, rotation time 0.5 sec/rotation, pitch 1.5, and slice thickness 1 mm. Examples of iodinated contrast agents include IOPAMIRON™ (Bayer HealthCare), which has iopamidol (generic name) as the active ingredient. For instance, 370 mg (95 mL) of Iopamiron may be injected at the rate of 4 mL/sec. A scan delay time of 20 sec may be used in case of early arterial phase (screening), about 30 sec for late arterial phase (detailed examination), and about 80 sec for portal venous phase (detailed examination) scanning. The dose of the x-ray is to be set according to the size of a patient.

The cancer lesion distribution image obtained by the use of nuclear magnetic resonance, i.e., the nuclear magnetic resonance image (MRI), can be captured by using, for instance, the MAGNETOM Symphony 1.5T (manufactured by Siemens AG) MRI system or similar equipment. The procedure for capturing image is not specifically restricted and exemplified by the following method. Firstly, before injection of the contrast agent, slice images along the three axis directions, i.e., coronal, sagittal, and transverse, are acquired under the static condition. Next, the contrast agent is injected, and dynamic imaging is carried out. More specifically, after deciding the imaging site, a bolus of the contrast agent is injected intravenously, and the changes with time in the three axis directions are captured at intervals of about 10 sec. In some cases the imaging may done along one axis direction only. Finally, after the lapse of sufficient time from the injection of the contrast agent, slice images along the three axis directions are captured as static contrast-enhanced images. Among these nuclear magnetic resonance images, the dynamic images are particularly effective for assessing the quality of a cancer lesion.

The cancer lesion distribution image obtained by the use of ultrasound, i.e., the ultrasound image, can be captured, for instance, using the digital diagnostic ultrasound system EUB-8500 (manufactured by Hitachi Medical Corporation) or similar equipment. The imaging frame rate and power level can be set by a person skilled in the art, based on the location, size, etc of the target organ.

Data on the accessory cancer lesion area is then collected from the two types of images obtained by the methods described above. In other words, data on the area detected by the near-infrared fluorescence intensity distribution image, but not detected in the cancer lesion distribution image is collected as the data on the accessory cancer lesion area.

The accessory cancer lesion area data can be identified by superimposing the near-infrared fluorescence intensity distribution image and the cancer lesion distribution image. Such superimposition can be done manually or by superimposing digital images. The two images can be compared, for instance, by identifying, from the cancer lesion distribution image, the organ wherein the main cancer lesion is present, and then determining the location of the identified organ in the near-infrared fluorescence intensity distribution image. In other words, the area detected in the near-infrared fluorescence intensity distribution image but not in the cancer lesion distribution image can be discovered. The data collection method of the present invention is particularly useful when the accessory cancer lesion is present in an organ that cannot be detected in the cancer lesion distribution image. However, the method can also be used for detecting a lesion (an accessory lesion) in parts that cannot be detected in the cancer lesion distribution image although the organ itself can be detected in that image. By using the data collection method of the present invention, a cancer lesion (an accessory lesion) with a long axis length of less than 5 mm can be detected.

Next, the accessory cancer lesion detector is described. In the above-described accessory cancer lesion detection method and data collection method, an accessory cancer lesion detector that comprises at least an irradiation means and an imaging means can be used for detecting an accessory cancer lesion during surgery for shrinking, destruction, or resection of a cancer lesion.

Figure 1:
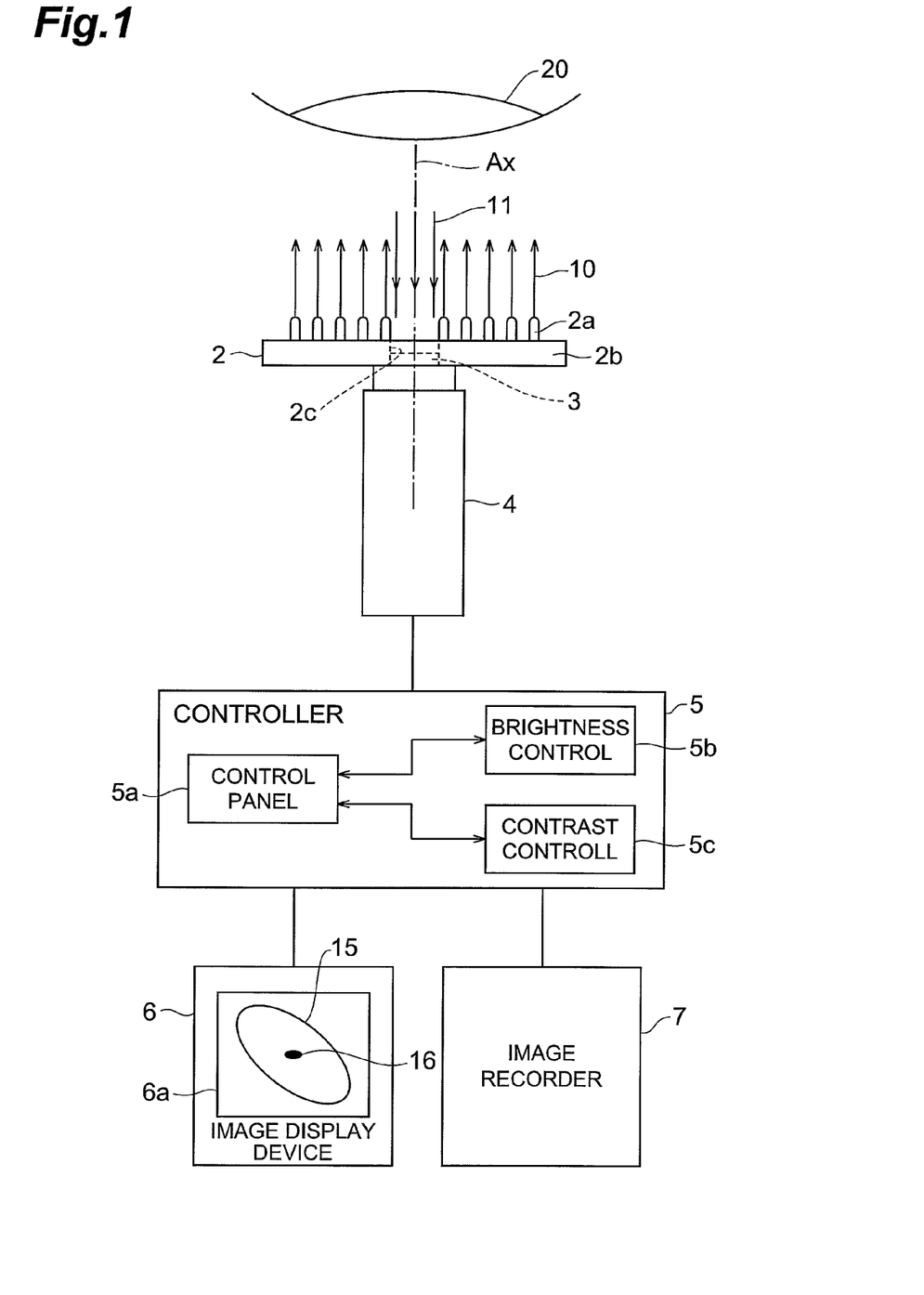
FIG. 1 is a configuration diagram of an embodiment of the accessory cancer lesion detector.
Figure 2:
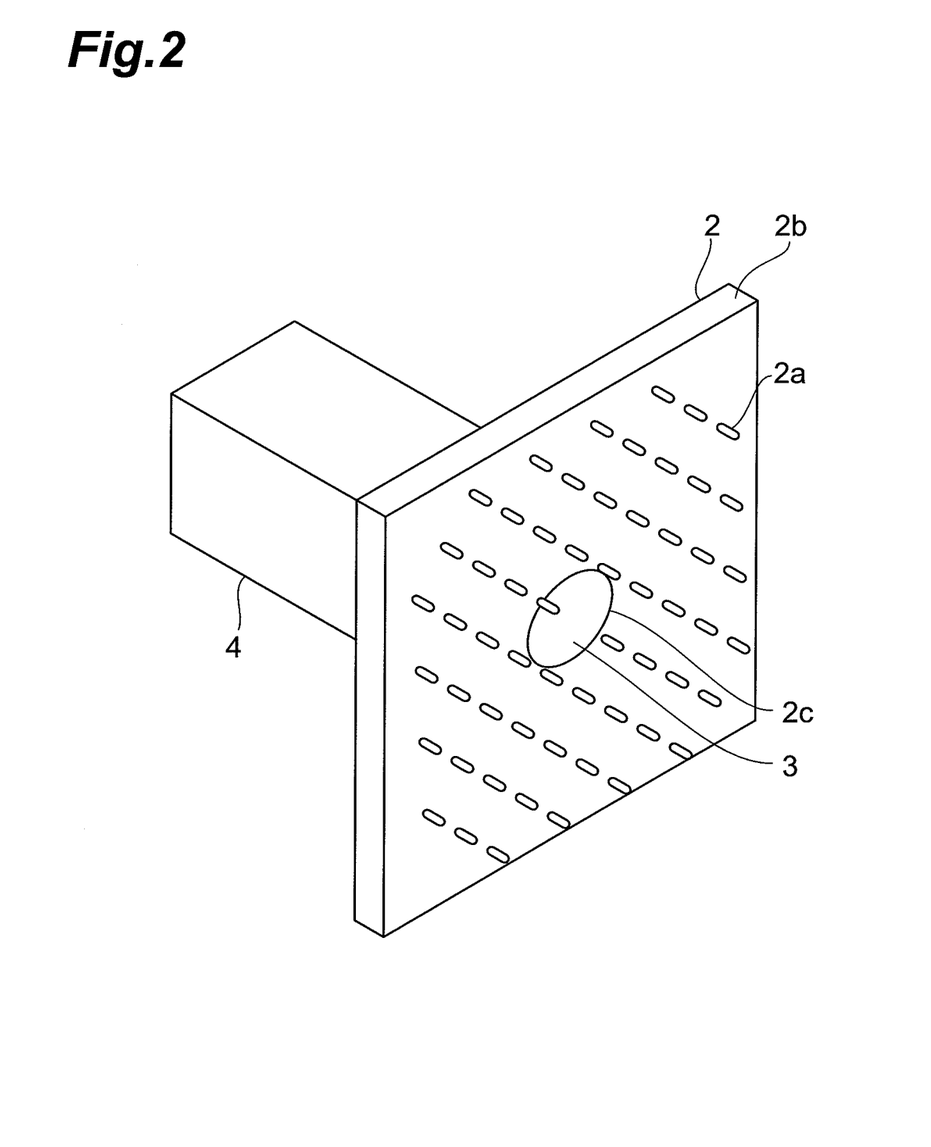
FIG. 2 is a perspective view showing the configuration of the excitation light source unit and imager used in the detector shown in FIG. 1.

FIG. 1 is a configuration diagram of an embodiment of such an accessory cancer lesion detector. FIG. 2 is a perspective view showing the configuration of the excitation light source unit and imager used in the accessory cancer lesion detector shown in FIG. 1.

The accessory cancer lesion detector of the embodiment shown in FIG. 1 irradiates the excitation light 10 of a certain wavelength on to the target organ 20, and observes the image created by the fluorescence (fluorescence image 11) emitted by the target organ 20, to detect the accessory cancer lesion. In the detection of an accessory cancer lesion using this detector, indocyanine green is injected beforehand at a point near the lesion in the target organ 20, or intravenously. Then, the near-infrared fluorescence coming from the indocyanine green accumulated in the accessory cancer lesion is observed to detect the accessory cancer lesion.

The accessory cancer lesion detector shown in FIG. 1 comprises the excitation light source unit 2 (irradiation means), optical filter 3, imager 4 (imaging means), controller 5, and image display device 6. The excitation light source unit 2 has a plurality of excitation light sources 2a, and a support 2b on one side whereof the excitation light sources 2a are installed. Each of the excitation light sources 2a comprises a light source that radiates light of the same wavelength as the excitation light, and is used to irradiate the target organ 20 with the excitation light 10. As shown in FIG. 2, the excitation light sources 2a are arranged two-dimensionally with symmetry about the central axis Ax of the excitation light source unit 2, which will become the optical axis of the detector.

As mentioned earlier, it is preferable to use semiconductor lasers (LD) or light emitting diodes (LED) as the excitation light sources 2a. The wavelength of the excitation light 10 supplied by the excitation light source 2a is suitably selected (760 nm for instance) from the near-infrared wavelength band, as the absorption band of indocyanine green is in that range.

An opening 2c is provided on the support 2b at its central location, which includes the central axis Ax. The opening 2c is provided for the passage of the fluorescence image 11, which comes from the target organ 20 towards the front of the excitation light source unit 2, to pass to its rear. The plurality of excitation light sources 2a described above is aligned 2-dimensionally to surround the opening 2c. In such a configuration, it is suitable to set the optical axes of those excitation light sources 2a located close to the opening 2c inclined towards the central axis Ax to prevent the intensity distribution of the excitation light 10 irradiated on to the target organ 20 from becoming weak at the center because of the effect of the opening 2c.

An optical filter 3 is installed in the opening 2c of the support 2b. This optical filter 3 allows the passage of light of the wavelength band of the fluorescence image 11 emitted by the accessory cancer lesions, out of the light coming from the target organ 20, which is the object of observation. A filter having transmission characteristics that cut off light of wavelengths other than that of the fluorescence image 11, which includes the excitation light 10 reflected back by the target organ 20, is preferably used as the optical filter 3.

The imager 4 is installed at the rear of the excitation light source unit 2. In this embodiment, the imager 4 is integrated with the excitation light source unit 2, with a common optical axis Ax. The fluorescence image 11 emitted by the fluorescent dye in an accessory cancer lesion, which is excited by the excitation light 10 irradiated by the excitation light sources 2a, passes through the opening 2c and the optical filter 3 of the support 2b, and arrives at the imager 4. The imager 4 captures the incoming fluorescence image 11 and outputs, as image data, the observed image thus obtained.

A CCD camera that can capture 2-dimensional images is used, for instance, as the imager 4. The imager preferably has the capability to capture, with high sensitivity, the light of the wavelength band of the fluorescence image 11 (the near-infrared wavelength band, as usually the target is a fluorescence image of about 800 nm). A power source for the excitation light sources and a power source for the imager are connected respectively as required with the plurality of excitation light sources 2a and the imager 4. The power sources, etc are not shown in FIG. 1. These devices can also be battery-driven.

A controller 5 is provided for the observed image output from the imager 4. The controller 5 is a means of manually or automatically controlling the image data of the observed image output by the imager 4. The controller 5 in this embodiment has a brightness control 5b and contrast control 5c, which respectively control the brightness and contrast of the observed image output by the imager 4. The control settings of the observed image, in the controls 5b and 5c, are input from the control panel 5a. The control panel 5a sets the control settings of the observed image automatically or through inputs from the viewer. If the control settings are fixed, there is no need to provide the control panel 5a. The transmission of image data from the imager 4 to the controller 5 can be through a cable, or wireless.

An image display device 6 and image recorder 7 are connected to the controller 5. The image display device 6 displays, on its display section 6a, the observed image 15 that has been controlled by the controller 5, as the image to be used for detecting an accessory cancer lesion. Examples of image display devices 6 include a CRT monitor and a liquid crystal display, attached to a CCD camera used as the imager 4. The image recorder 7 is a means of recording the observed image data controlled by the controller 5. Examples of devices that can be used as the image recorder 7 include a videotape recorder that records the observed image on videotape, a recording medium.

Now the method of detecting an accessory cancer lesion using the accessory cancer lesion detector illustrated in FIG. 1 is described. First, the fluorescent dye indocyanine green is injected intravenously. After the lapse of a certain time (typically 1 to 10 days from the intravenous injection), when excitation light 10 of a certain wavelength (760 nm for instance) is irradiated on the target organ 20 from the excitation light source unit 2, a fluorescence image 11 in the near-infrared wavelength band is emitted by the accessory cancer lesion because of the indocyanine green. Here, the optical filter 3 allows the passage of the fluorescence image 11 while cutting off the reflected light coming from the target organ 20 that is being irradiated by the excitation light 10.

The fluorescence image 11 that passes through the optical filter 3 is captured by the CCD camera used as the imager 4, and the data of the observed image is output from the CCD camera to the controller 5. The controller 5 controls the brightness and contrast of the observed image coming from the imager 4. As a result, the observed image 15 (which includes the image of the main cancer lesion) containing the accessory cancer lesion image 16 is generated. When such an image is displayed on the display section 6a of the image display device 6, the detection of the accessory cancer lesion is realized. Furthermore, if necessary, the observed image 15 is recorded on a recording medium in the image recorder 7.

The accessory cancer lesion area data can be collected by comparing the near-infrared fluorescence intensity distribution image, obtained as described above, with the cancer lesion distribution image obtained by the use of x-rays, nuclear magnetic resonance, or ultrasound on the target organ 20 before administering the indocyanine green.

EXAMPLES

The present invention will now be described in more specific terms, citing some examples of the present invention. However, these examples in no way restrict the scope of the invention, and various modifications can be made within the technical scope of the present invention.

In the examples 1 to 5 given below, the ICG (0.5 mg/kg) was injected intravenously a few days before the surgery. In other words, in the examples 1, 2, 3, 4, and 5, the intravenous ICG injection was administered, respectively, 4, 4, 8, 1, and 4 days before the surgery. The liver was observed with the infrared camera system PDE (Photodynamic Eye (trade name), Hamamatsu Photonics K.K.) having the configuration shown in FIGS. 1 and 2, used as the accessory cancer lesion detector, and hepatocellular carcinoma was detected. In examples 1 to 4, the cancer was primary liver cancer, and in Example 5 it was metastatic liver cancer.

Example 1

Figure 3:
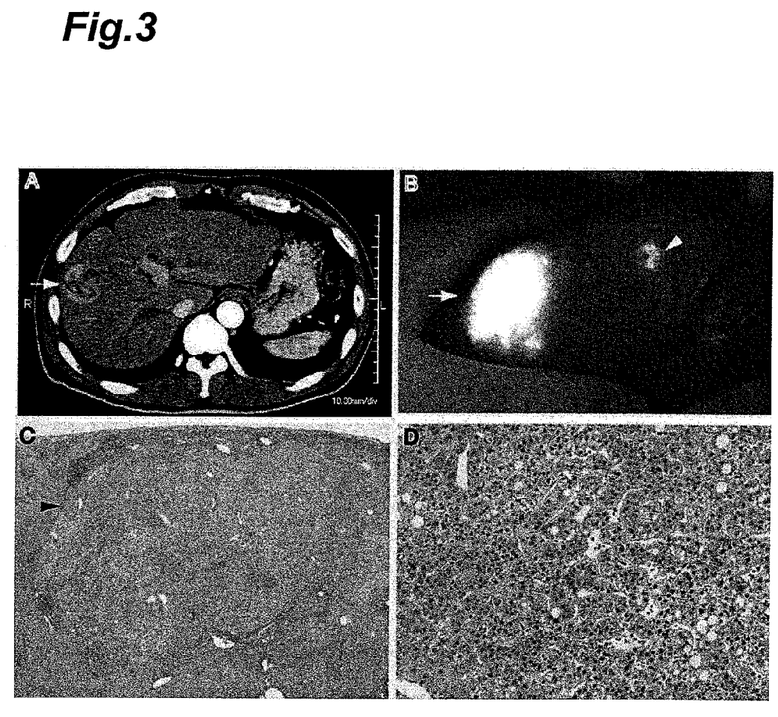
FIG. 3 shows images of a cancer lesion obtained by contrast CT and the ICG fluorescence method, and micrographs of a cancer lesion; 3A is an image obtained by contrast CT, 3B is a near-infrared fluorescence intensity distribution image from ICG in the liver, 3C is a micrograph of a tissue section of an accessory lesion, and 3D is a magnified image of the micrograph of 3C.

Example 1 was a case of a male in his 50s. Preoperative contrast CT detected the presence of a single HCC, 40 mm in diameter, in the S5/8 segment of the liver. FIG. 3A is an image showing the result of contrast CT. The arrow indicates the HCC. When the patient's abdomen was cut open and intraoperative diagnosis was carried out with the PDE, a fluorescent area, 5 mm in diameter, was detected in the S4 segment of the liver, in addition to the main tumor (main lesion). Therefore, this part (the accessory lesion) was also resected. FIG. 3B is a near-infrared fluorescence intensity distribution image (measured after the abdomen was opened but before the resection) from ICG in the liver. The arrow (arrowhead) at right indicates the fluorescent area (accessory lesion), 5 mm in diameter, in the S4 segment of the liver. The larger fluorescent area, indicated by the arrow on the left, is the main tumor area (main lesion). Based on histological tests on the resected tissue, the main tumor was diagnosed as moderately differentiated HCC, and the accessory lesion detected in the S4 segment of the liver was diagnosed as highly differentiated HCC. FIG. 3C is a micrograph of a tissue section of the accessory lesion (fluorescent area, 5 mm in diameter, in the S4 segment of the liver), and FIG. 3D is a magnified image of the micrograph of FIG. 3C.

Example 2

Figure 4:
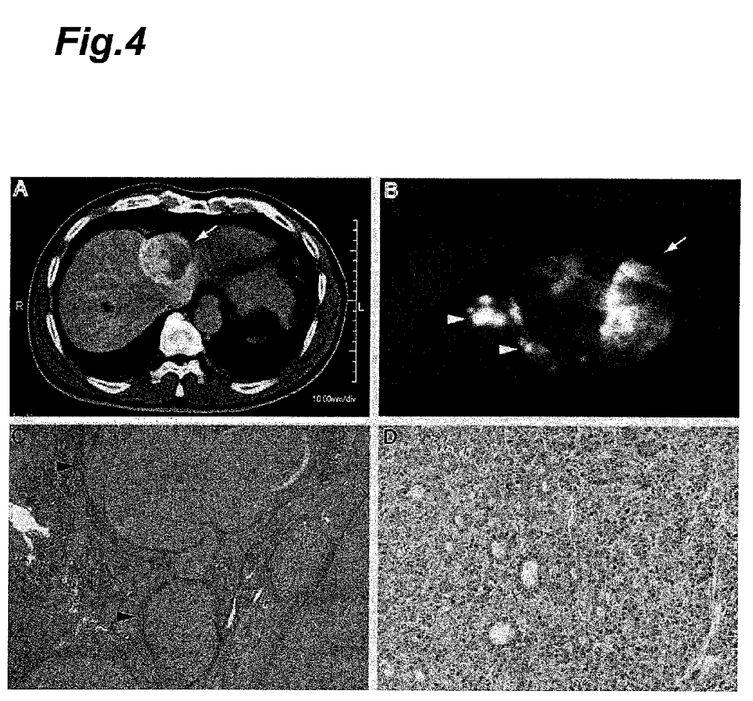
FIG. 4 shows images of a cancer lesion obtained by contrast CT and the ICG fluorescence method, and micrographs of a cancer lesion; 4A is an image obtained by contrast CT, 4B is a near-infrared fluorescence intensity distribution image from ICG in the liver, 4C is a micrograph of a tissue section of an accessory lesion, and 4D is a magnified image of the micrograph of 4C.

Example 2 was a case of a male in his 70s. Preoperative contrast CT detected the presence of a single HCC, 45 mm in diameter, in the S2/3/4 segment of the liver. FIG. 4A is an image showing the result of contrast CT. The arrow indicates the HCC. From the contrast CT image, the HCC was diagnosed to be simple nodular type. But after opening of the abdomen, and intraoperative diagnosis using the PDE, some fluorescent areas (accessory lesions), 2 to 3 mm in diameter, were detected scattered around the main tumor (main lesion). Therefore, the area to be resected was made to include these, and the resection was carried out. FIG. 4B is a near-infrared fluorescence intensity distribution image (measured after the abdomen was opened but before the resection) from ICG in the liver. The fluorescent area indicated by the arrow at right is the main tumor area (main lesion). The two arrows (arrowheads) at left indicate fluorescent areas (accessory lesions), 2 to 3 in mm diameter, seen around the main tumor. Based on histological tests on the resected tissue, the main tumor was diagnosed to be a moderately differentiated HCC, and the scattered nodules (accessory lesions) were diagnosed to be satellite nodules of simple nodular HCC with extranodular growth. FIG. 4C is a micrograph of a tissue section of an accessory lesion (fluorescent area, 2 to 3 mm in diameter seen around the main tumor), and FIG. 4D is a magnified image of the micrograph of FIG. 4C.

Example 3

Figure 5:
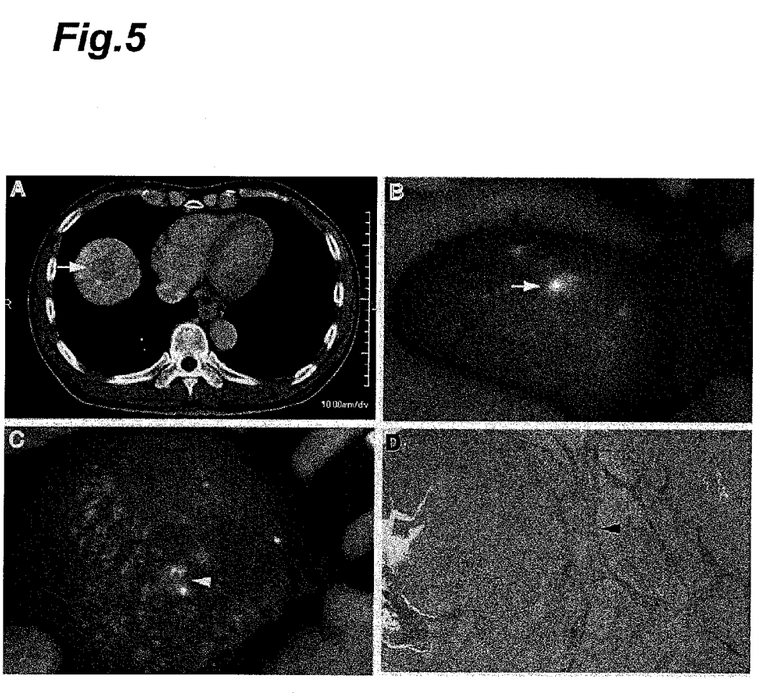
FIG. 5 shows images of a cancer lesion obtained by contrast CT and the ICG fluorescence method, and micrographs of a cancer lesion; 5A is an image obtained by contrast CT, 5B and 5C are near-infrared fluorescence intensity distribution images from ICG in the liver, and 5D is a micrograph of a tissue section of an accessory lesion.

Example 3 was a case of a male in his 60s. Preoperative contrast CT detected the presence of a single HCC, 25 mm in diameter, in the S8 segment of the liver. FIG. 5A is an image showing the result of contrast CT. The arrow indicates the HCC. When the abdomen was opened, the surface of the liver was found to be irregular. Therefore, the identification of the main tumor (main lesion) by intraoperative ultrasonography diagnosis was difficult. But intraoperative diagnosis using the PDE could confirm the HCC areas (main and accessory lesions) as fluorescent areas, which made it easy to decide the area to be resected. FIG. 5B and FIG. 5C are near-infrared fluorescence intensity distribution images (measured after the abdomen was opened but before the resection) from ICG in the liver. The arrow in FIG. 5B indicates the main tumor (main lesion), and the arrow (arrowhead) in FIG. 5C indicates a fluorescent area (accessory lesion), 5 mm in diameter, in the S5 segment of the liver. Based on these measurements, the fluorescent area (accessory lesion), 5 mm in diameter, in the S5 segment of the liver was also resected in addition to the main tumor (main lesion). Based on histological tests on the resected tissue, the main tumor (main lesion) was diagnosed to be a highly differentiated HCC, and the accessory lesion in the S5 segment was diagnosed as slightly less differentiated HCC than the main tumor. FIG. 5D is a micrograph of the accessory lesion (arrowhead).

Example 4

Figure 6:
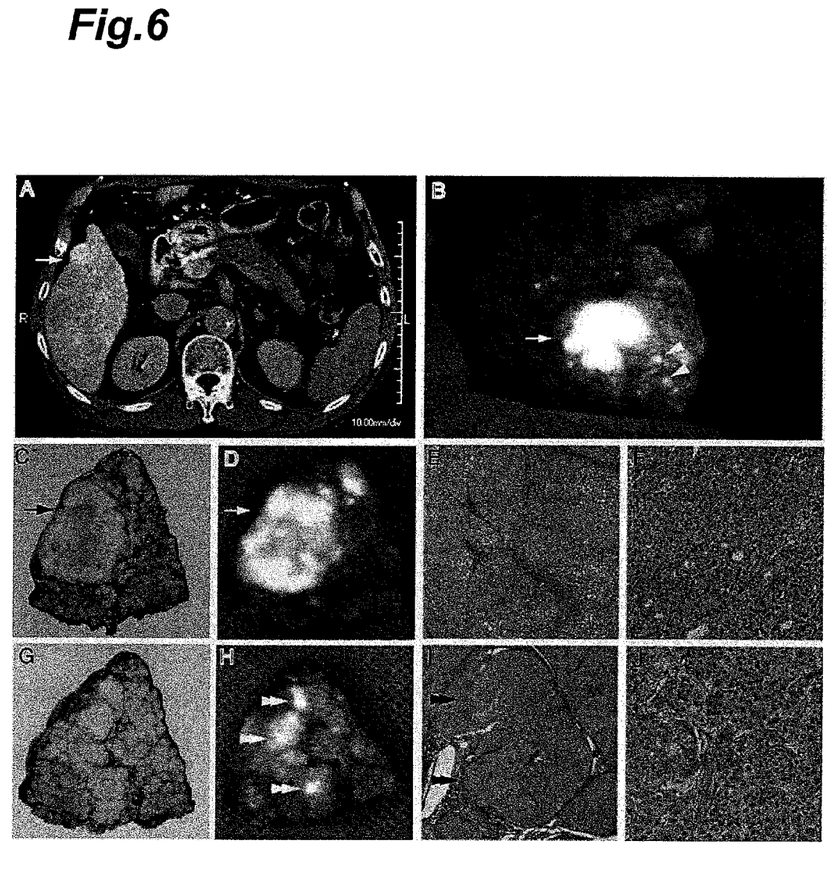
FIG. 6 shows images of a cancer lesion obtained by contrast CT and the ICG fluorescence method, photographs of a resected cancer lesion, and micrographs of a cancer lesion; 6A is an image obtained by contrast CT, 6B is a near-infrared fluorescence intensity distribution image from ICG in the liver, 6C and 6G are photographs of formalin-fixed liver, 6D and 6H are near-infrared fluorescence intensity distribution images from ICG in the resected liver (they respectively correspond to 6C and 6G), and 6E, 6F, 6I, and 6J are micrographs of lesion tissue (6F is a magnified image of 6E and 6J is a magnified image of 6I)

Example 4 was a case of a male in his 70s. Preoperative contrast CT detected the presence of a single HCC, 25 mm in diameter, in the S5 segment of the liver. FIG. 6A is an image showing the result of contrast CT. The arrow indicates the HCC. When the abdomen was opened, the surface of the liver was found to be irregular, and the identification of the main tumor by intraoperative ultrasonography diagnosis was difficult. But intraoperative diagnosis by the PDE could confirm the HCC areas (main and accessory lesions) as fluorescent areas, which made it easy to decide the area to be resected. FIG. 6B is a near-infrared fluorescence intensity distribution image (measured after the abdomen was opened but before the resection) from ICG in the liver. The fluorescent area indicated by the arrow at left is the main tumor area (main lesion), and the two arrows (arrowheads) on the right indicate fluorescent areas (accessory lesions), 3 mm in diameter, observed around the main tumor. Based on the above measurements, more than one fluorescent area (accessory lesions), each 3 mm in diameter, were resected in addition to the main tumor (main lesion). Further, the resected liver was fixed in formalin and made into 3 mm thick slices (FIG. 6C and FIG. 6G), and the cross-sections observed with the PDE (FIG. 6D and FIG. 6H). Based on histological test of the part corresponding FIG. 6C and FIG. 6D, the main tumor and the scattered nodules were diagnosed as highly differentiated HCC. FIG. 6E is a micrograph of a tissue section of an accessory lesion (fluorescent area, 3 mm in diameter), and FIG. 6F is a magnified image of the micrograph of FIG. 6E. The near-infrared fluorescence intensity distribution image of the part corresponding the area shown in FIG. 6G (FIG. 6H) revealed light emission from areas where no nodule was detected macroscopically (double arrowheads in FIG. 6H). Based on histological test of the areas indicated by the double arrowheads in FIG. 6H, these areas were also diagnosed as highly differentiated HCC. FIG. 6I is a micrograph of tissue section showing these parts, and FIG. 6J is a magnified image of the micrograph of FIG. 6I.

Example 5

Figure 7:
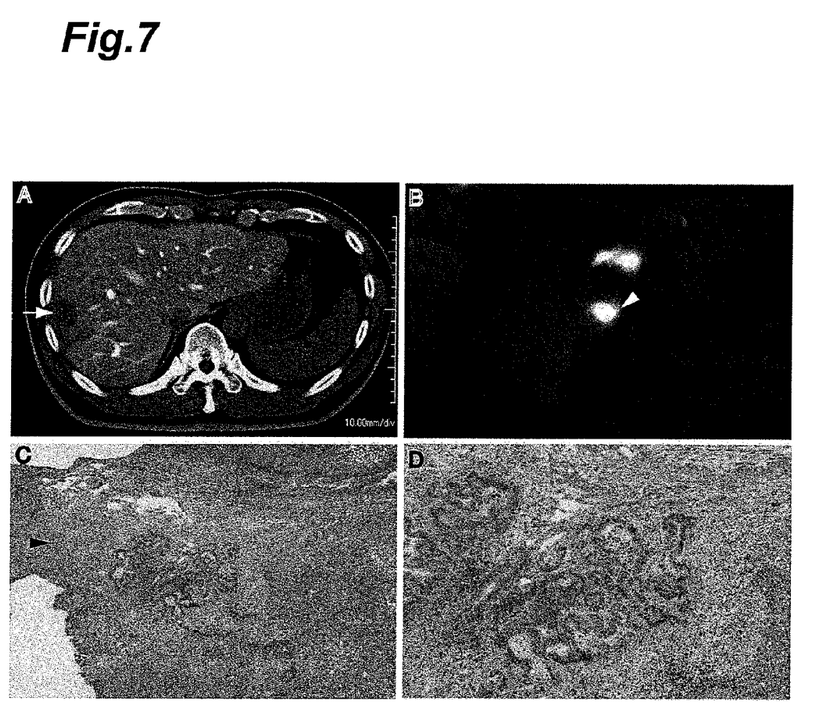
FIG. 7 shows images of a cancer lesion obtained by contrast CT and the ICG fluorescence method, and micrographs of the cancer lesion; 7A is an image obtained by contrast CT, 7B is a near-infrared fluorescence intensity distribution image from ICG in the liver, 7C is a micrograph of a tissue section of an accessory lesion, and 7D is a magnified image of the micrograph of 7C.

Example 5 was a case of a male in his 50s. Preoperative contrast CT detected the presence of a liver tumor, 25 mm in diameter, in the S2 segment and a liver tumor, 22 mm in diameter, in the S7 segment of the liver. FIG. 7A is an image showing the result of contrast CT. The arrow indicate liver tumor. When the abdomen was opened, and the PDE was used intraoperatively, apart from the two lesions identified before the surgery, a fluorescent area (accessory lesion), 5 mm in diameter, was also detected in the S4 segment of the liver, which was difficult to identify definitely by palpation or intraoperative ultrasonography. Therefore, all these areas were included in the area to be resected, and liver resection performed. FIG. 7B is a near-infrared fluorescence intensity distribution image (measured after the abdomen was opened but before the resection) from ICG in the liver. The arrow (arrowhead) indicates a fluorescent area (accessory lesion), 5 mm in diameter. Histological test of the resected tissue confirmed that it had adenocarcinoma, which was diagnosed as metastasis of colon cancer into the liver. FIG. 7C is a micrograph of a tissue section of the accessory lesion (fluorescent area, 5 mm in diameter), and FIG. 7D is a magnified image of the micrograph of FIG. 7C.

In all the cases examined, minute HCC or metastatic cancers, which could not be confirmed by conventional contrast CT, could be discovered by intraoperative diagnosis with a PDE. Such minute HCC or metastatic cancers were the ones that would have been missed in conventional hepatectomy. Such missing is believed to be one of the reasons for the poor 5-year recurrence-free survival.

The ICG infrared camera system described above would be useful not only for intraoperative detection of minute HCC and metastatic cancer but also for determining the liver resection line, and for modifying the surgical technique.

What is claimed is:

1. A method of detecting an accessory cancer lesion, comprising:
   an administration step wherein indocyanine green is administered to a living body,
   an irradiation step wherein a target organ suspected of having cancer is surgically exposed and irradiated with excitation light of indocyanine green,
   an imaging step wherein a near-infrared fluorescence intensity distribution image from the excited indocyanine green in the target organ is obtained, and
   an identification step wherein an area having the near-infrared fluorescence in the intensity distribution image, excluding a main cancer lesion detected in preoperative examination or intraoperative macroscopic observation, is identified as an accessory cancer lesion in the target organ and wherein the imaging step is carried out 1 to 10 days after the administration step.

2. The method of detecting an accessory cancer lesion according to claim 1 wherein the preoperative examination is by x-ray imaging, nuclear magnetic resonance imaging, or ultrasonographic imaging of the target organ.

3. The method of detecting an accessory cancer lesion according to claim 1 wherein the indocyanine green is administered through intravenous injection in the administration step.

4. The method of detecting an accessory cancer lesion according to claim 1 wherein the indocyanine green used in the administration step is neither complexed with a high density lipoprotein nor bound to antibodies against proteins that are specifically present in the accessory lesion.

5. The method of detecting an accessory cancer lesion according to claim 1 wherein the cancer is primary liver cancer or metastatic liver cancer.

6. The method of detecting an accessory cancer lesion according to claim 1 wherein the living body is a living body of human or non-human mammal.

7. A method of treating cancer wherein an area containing at least one accessory lesion identified by the method of detecting an accessory cancer lesion according to claim 1 is shrunk, destroyed or resected.

8. The method of treating cancer according to claim 7 wherein the main cancer lesion detected in the preoperative examination or the intraoperative macroscopic observation is shrunk, destroyed, or resected along with the accessory lesion area.

* * * * *